United States Patent [19]

Parrish et al.

[11] Patent Number: 5,037,860
[45] Date of Patent: Aug. 6, 1991

[54] FLEXIBLE POLYURETHANE FOAM PREPARED USING 1,1,1-TRICHLOROETHANE AS A BLOWING AGENT

[75] Inventors: Donald B. Parrish, Lake Jackson; Lenore F. Oswald, Angleton; Raymond E. Thomas, Lake Jackson, all of Tex.

[73] Assignee: The Dow Chemical Company, Midland, Mich.

[21] Appl. No.: 559,544

[22] Filed: Jul. 17, 1990

Related U.S. Application Data

[63] Continuation of Ser. No. 364,930, Jun. 12, 1989, abandoned.

[51] Int. Cl.$^5$ .............................................. C08G 18/14
[52] U.S. Cl. ...................................... 521/110; 521/131
[58] Field of Search ................................ 521/110, 131

[56] References Cited

U.S. PATENT DOCUMENTS 4,742,089  5/1988  Naka et al. ........................... 521/131

OTHER PUBLICATIONS

PCT, WO89/00594, 1/26/89.

Primary Examiner—Maurice J. Welsh

[57] ABSTRACT

Flexible foam is prepared using 1,1,1-trichloroethane as the sole or predominant auxiliary blowing agent.

21 Claims, No Drawings

FLEXIBLE POLYURETHANE FOAM PREPARED USING 1,1,1-TRICHLOROETHANE AS A BLOWING AGENT

This is a continuation in part, of application Ser. No. 364,930 filed June 12, 1989 and now abandoned.

BACKGROUND OF THE INVENTION

This invention relates to flexible polyurethane foam and methods for its preparation.

Polyurethane foams are widely used in many packing, cushioning and other applications. These foams are usually prepared by reacting a polyisocyanate with a relatively high equivalent weight active hydrogen-containing composition in the presence of a blowing agent. In most commercial foam formulations, water is used as a primary blowing agent, and low boiling halocarbons are used as "auxiliary" blowing agents. These auxiliary blowing agents contribute gases which cause the polymer to expand into a cellular structure. In addition, they soften the foam and during processing act as a heat sink, thereby preventing the exotherm from the polymerization reaction from degrading the polymer.

The most common auxiliary blowing agents are low boiling hard chlorofluorocarbons (CFCs) such as CFC-11 and CFC-12, which in recent years have been attacked as contributing to the destruction of the ozone layer of the atmosphere. Accordingly, the continued use of these hard CFCs is being increasingly restricted. For this reason, it is desirable to provide alternatives to these hard CFC blowing agents.

However, because of the several roles the auxiliary blowing agents play in the preparation of polyurethane foam, it has been difficult to find acceptable substitutes. Many potential substitutes are prohibitively expensive. Others present unacceptable fire or toxicological risks. Many other potential substitutes provide blowing, but fail to adequately soften the foam or absorb enough of the reaction exotherm.

Thus, it is desired to provide a blowing agent for flexible polyurethane foam which performs the functions of conventional auxiliary blowing agents, yet is safe and affordable.

SUMMARY OF THE INVENTION

This invention is a process for preparing flexible polyurethane foam by reacting a reaction mixture comprising a polyisocyanate and a relatively high equivalent weight active hydrogen-containing material in the presence of a volatile blowing agent, wherein at least about 85 mole percent of said volatile blowing agent is 1,1,1-trichloroethane.

In another aspect, this invention is a process for preparing flexible foam by reacting a reaction mixture comprising a polyisocyanate and a relatively high equivalent weight active hydrogen-containing material in the presence of a volatile blowing agent, wherein the volatile blowing agent is a mixture of at least about 50 weight percent 1,1,1-trichloroethane, from about 0-50 weight percent ethyl chloride or methylene chloride or mixtures thereof, and from about 0-15 weight percent of another volatile blowing agent.

In this invention, 1,1,1-trichloroethane is used as the sole or predominant volatile blowing agent. It can be used as the only blowing agent, or as an auxiliary blowing agent in water-blown foam formulations. The ability to prepare flexible foam using 1,1,1-trichloroethane as the sole or predominant volatile blowing agent is quite surprising, due to its high (~74.1° C.) boiling point. Heretofore, it has been believed that the use of such high boiling compounds would not be suitable for preparing good quality flexible foam, unless a significant quantity of a low boiling hydrocarbon such as CFC-22 was also present.

In addition, the foam prepared in accordance with this invention has properties which are largely similar to those foams prepared using conventional volatile blowing agents, which is again surprising in view of the substantial difference in boiling point of the blowing agent, and the previous difficulties in finding alternative auxiliary blowing agents.

DETAILED DESCRIPTION OF THE INVENTION

As used herein, the term "volatile blowing agent" means an organic compound which has a boiling point of at least about $-15°$ C. (at 1 atmosphere pressure) but at or below the maximum temperatures generated during the reaction of the reaction mixture to form a foam.

In one aspect of this invention, at least about 5 mole percent of the volatile blowing agent is 1,1,1-trichloroethane. In this aspect, it is more preferred that at least about 90 mole percent of the volatile blowing agent is 1,1,1-trichloroethane, and especially preferred that essentially all of the volatile blowing agent, except for minor impurities, is 1,1,1-trichloroethane.

In a second aspect of this invention, at least about 50 weight percent of the volatile blowing agent is 1,1,1-trichloroethane, about 0 to about 50 weight percent thereof is methylene chloride and/or ethyl chloride, and about 0 to about 15 weight percent is another volatile blowing agent.

In the first aspect of this invention, the other volatile blowing agent is ethyl chloride, methylene chloride, or any of the other blowing agents described in the following paragraphs.

In the second aspect of this invention, the other volatile blowing agent, i.e., that comprising about 0 to about 15 weight percent of the mixture, includes any organic compound which does not undesirably react with the other components in the reaction mixture and has a boiling point as described before. Preferred, however, are alkanes having from about 4 to about 10, preferably about 5 to about 8 carbon atoms, and partially or fully halogenated alkanes having from 1 to about 5, preferably about 1 to about 3 carbon atoms. Among these, CFC-11, CFC-113, CFC-114, CFC-123, CFC-123a, CFC-124, CFC-124a, CFC-133 (all isomers), CFC-134, CFC-134a, CFC-141b, CFC-142, CFC-151, pentane, heptane, hexane, perhalogenated propanes and the like are suitable. Similar alkanes containing bromine atoms are also useful. Among those listed, the "soft" CFCs (those having at least one hydrogen atom) are preferred when another volatile blowing agent is used. CFC-123, CFC-141b and CFC-142 are especially preferred.

In particularly preferred embodiments of the invention, 1,1,1-trichloroethane is the sole volatile blowing agent, or 1,1,1-trichloroethane is in admixture with up to 50, especially up to about 30, weight percent methylene chloride or ethyl chloride, and no additional volatile blowing agent is used. It is most preferred to use 1,1,1-trichloroethane as the sole volatile blowing agent.

The 1,1,1-trichloroethane, as well as the other volatile blowing agents, may contain stabilizers such as butylene oxide which reduce its susceptibility to degradation when exposed to water or other conditions under which 1,1,1-trichloroethane tends to decompose.

The blowing agent used herein can be used in substantially the same manner as conventional volatile blowing agents. To obtain an equivalent quantity of generated gas, the same amount of this blowing agent is used, on a molar basis, as are conventional volatile blowing agents. However, because 1,1,1-trichloroethane has a greater molecular weight than many conventional blowing agents, a greater weight thereof is generally used.

In this invention, a polyisocyanate is reacted with at least one relatively high equivalent weight active hydrogen-containing material in the presence of the volatile blowing agent described before. The term "relatively high equivalent weight active hydrogen-containing material" is used herein to refer to a material having an average of at least two active hydrogen-containing groups per molecule and an equivalent weight of about 400 or higher. Equivalent weight, for the purposes of this invention, is the molecular weight of the material divided by its average number of active hydrogen-containing groups per molecule. The active hydrogen-containing groups can be primary or secondary hydroxyl, primary or secondary amine, thiol, carboxylic acid, or other groups which react with an isocyanate to form a covalent bond therewith. Among these, the hydroxyl and amine groups are preferred, as discussed further hereinafter. For convenience herein, all these relatively high equivalent weight materials, regardless of their particular active hydrogen-containing groups, are referred to herein as "polyols". All materials made from such "polyols" and a polyisocyanate are referred to herein for convenience as "polyurethanes".

Suitable polyols include those materials of at least about 400 equivalent weight as described in columns 3-5 of U.S. Pat. No. 4,581,418, incorporated herein by reference. Preferred on the basis of performance, availability and cost are polyethers and polyesters, with polyethers being more preferred. Of the polyethers, preferred are polymers and copolymers of propylene oxide, preferably those containing at least 30, more preferably at least about 50, and most preferably at least about 70 weight percent oxypropylene units. Dispersions of polymer particles in a polyol (polymer polyols), such as described in U.S. Pat. Nos. 4,581,418, 4,460,715, 3,953,393, 4,374,209 and 4,324,716, are also useful herein and often preferred.

It is also preferred that the polyol have an average nominal functionality (average number of active hydrogen-containing groups per molecule) from about 2 to about 6, more preferably about 2 to about 4, most preferably about 2 to about 3. "Nominal functionality" refers to the average number of active hydrogen-containing groups per molecule in the initiator used in preparing the polyol.

The choice of polyol depends somewhat on the type of foam being prepared. In making slabstock foam, the polyol preferably has an equivalent weight from about 800 to about 2500, more preferably about 800 to about 1300, and the active hydrogen groups are preferably primary or secondary hydroxyl groups, with secondary hydroxyl groups or mixtures of primary or secondary hydroxyl groups being most preferred. The use of polymer polyols is also preferred in slabstock foam to promote cell opening and provide improved load bearing.

In making molded foam, it is preferred to use higher equivalent weight and more reactive polyols. Thus, the equivalent weight of the polyol is preferably from about 1000 to about 2500, preferably about 1200 to about 2000. Primary or secondary aromatic amine groups, secondary aliphatic amine groups and primary hydroxyl groups are the preferred active hydrogen containing groups. Polyols containing a mixture of at least about 75% primary hydroxyl groups and up to about 25 percent secondary hydroxyl groups are most preferred on the basis of cost and availability. The preparation of flexible foam using relatively high equivalent weight amine-terminated materials is discussed in copending application Ser. No. 170971, now U.S. Pat. No. 4,845,133 incorporated herein by reference. Polymer polyols can also be used in preparing molded foam. The most preferred polyols for molded foam are the nominally di- or trifunctional poly(propylene oxide)s which are end-capped with about 10 to about 20 weight percent ethylene oxide, and polymer polyols having such polyols as the continuous phase.

Either aliphatic or aromatic polyisocyanates can be used in this invention to make foam. Suitable aliphatic polyisocyanates include ethylene diisocyanate, 1,4-tetramethylene diisocyanate, 1,6-hexamethylene diisocyanate, 1,12-dodecane diisocyanate, cyclobutane-1,3-diisocyanate, cyclohexane-1,3- and -1,4-diisocyanate, 1,5-diisocyanate-3,3,5-trimethylcyclohexane, 25 2,4- and/or 2,6-hexahydrotoluene diisocyanate, perhydro-2,4'- and/or -4,4'-diphenylmethanediisocyanate ($H_{12}MDI$); isophorone diisocyanate, and the like.

Suitable aromatic polyisocyanates include, for example, 2,4- and/or 2,6-toluene diisocyanate (TDI), 2,4'-diphenylmethanediisocyanate, 1,3- and 1,4-phenylene diisocyanate, 4,4'-diphenylmethane diisocyanate (including mixtures thereof with minor quantities of the 2,4'-isomer), 1,5-naphthylene diisocyanate, triphenylmethane-4,4',4'-triisocyanate, polyphenylpolymethylene polyisocyanates, mixtures thereof and the like.

In addition, derivatives and prepolymers of the foregoing polyisocyanates such as those containing urethane, carbodiimide, allophanate, isocyanurate, acylated urea, biuret, ester and similar groups are useful herein. Of these, prepolymers of TDI and MDI, and the so-called "liquid MDI" products which contain carbodiimide groups and have an equivalent weight of about 130-150 are of particular significance.

Of the foregoing polyisocyanates, TDI, MDI, isophorone diisocyanate, $H_{12}MDI$, hexamethylene diisocyanate, cyclohexane diisocyanate, their derivatives and mixtures thereof are preferred due to their cost, commercial availability and performance. TDI, MDI and derivatives of MDI are more preferred. TDI, particularly mixtures of the 2,4- and 2,6- isomers, is especially preferred.

The polyisocyanate is advantageously used in an amount sufficient to provide an isocyanate index of about 90 to about 130, preferably about 95 to about 115, more preferably about 100 to about 110. The term "isocyanate index" is used herein to mean 100 times the ratio of isocyanate groups to active hydrogen equivalents present in the reaction mixture. At higher indices, the excess polyisocyanate groups tend to trimerize, thereby reducing the flexibility of the foam. At lower indices, inadequate curing may be obtained, with a loss of physical properties.

In addition to the polyisocyanate, volatile blowing agent and polyol, various other components may be used in the reaction mixture. The selection of these addition components depends to a large extent on the type of foam, and its intended end use and properties.

In many foams, water is used to provide primary gas generation and to form polyurea linkages in the polymer. When used, water is generally present in an amount from about 0.5 to about 12, preferably about 1 to about 8 parts per 100 parts by weight polyol. Increasing the amount of water tends to reduce the density of the foam. For preparing foam having a density of about 1-2 pounds/cubic foot (pcf), more preferably about 3 to about 8, most preferably about 4-6 parts of water are used per 100 parts by weight polyol. For preparing foam having a density of about 2-3 pcf, about 2 to about 5 parts by weight water are most preferred. The use of water is preferred in preparing most foam except some integral skin foams, where water is often omitted from the formulation in order to facilitate the formation of a substantially non-cellular skin on the foam.

The volatile blowing agent of this invention is used in an amount sufficient to provide the desired additional density reduction (beyond that supplied by the water, when present), soften the foam and moderate temperatures inside the reacting mixture. In order to perform the last two functions, the amount of volatile blowing agent often increases with increasing water, as increasing the water also increases the reaction exotherm and the amount of polyurea linkages in the foam, which cause the foam to be hard. Advantageously, about 3 to about 50, preferably about 5 to about 45 parts by weight of the volatile blowing agent are used per 100 parts by weight polyol. For preparing 1-2 pcf foam with 3-8 parts water, it is preferred to use about 2 to about 40, more preferably about 5 to about 40 parts volatile blowing agent per 100 parts by weight polyol. In preparing 2-3 pcf foam with about 2-5 parts water, it is preferred to use about 2 to about 30, more preferably about 3 to about 25 parts volatile blowing agent per 100 parts polyol.

A catalyst for the reaction of the poly(propylene oxide) polymer and the polyisocyanate is also advantageously used in making foam according to this invention. Although a wide variety of materials are known to be useful for this purpose, the most widely used and preferred catalysts are the tertiary amine catalysts and the organometallic catalysts.

Exemplary tertiary amine catalysts, include, for example, triethylenediamine, N-methyl morpholine, N-ethyl morpholine, diethyl ethanolamine, N-coco morpholine, 1-methyl-4-dimethylaminoethyl piperazine, 3-methoxy-N-dimethylpropylamine, N,N-diethyl-3-diethylaminopropylamine, dimethylbenzyl amine, bis(2-dimethylaminoethyl)ether, and the like. Tertiary amine catalysts are advantageously employed in an amount from about 0.01 to about 5, preferably about 0.03 to about 2 parts per 100 parts by weight of the polyol.

Exemplary organometallic catalysts include organic salts of metals such as tin, bismuth, iron, mercury, zinc, lead and the like, with the organotin compounds being preferred. Suitable organotin catalysts include dimethyltindilaurate, dibutyltindilaurate, stannous octoate and the like. Other suitable catalysts are taught, for example, in U.S. Pat. No. 2,846,408. Advantageously, about 0.001 to about 3 parts by weight of an organometallic catalyst is used per 100 parts of polyol.

In order to make a stable foam, i.e., one which does not collapse or contain significant quantities of large pores, a surfactant may be used to stabilize the foaming reaction mixture against collapse until the mixture is sufficiently cured to maintain its cellular configuration. Suitable surfactants include siloxane/poly(alkylene oxide) copolymers as described, for example, in U.S. Pat. Nos. 3,887,500 and 3,957,842 as well as certain fatty acid salts. The selection and use of such surfactants in preparing foams is well-known in the art. Since an excess of surfactant tends to cause the reaction mixture to collapse before gelling, it is preferred to use a surfactant in an amount less than about 5, preferably less than about 2 parts per 100 parts of polyol.

Crosslinkers and chain extenders may be used, particularly in making molded foam or high resiliency slabstock foam, in order to improve load-bearing and processing. Suitable such crosslinkers include alkanolamines and other compounds of about 200 or lower equivalent weight having about 3-8, preferably about 3-4 active hydrogen-containing groups per molecule. Exemplary such compounds are glycerine and trimethylolpropane, alkoxylated derivatives thereof, as well as other alkylene triols. Preferred, however, are alkanolamines such as diethanolamine, triisopropanolamine, triethanolamine, diisopropanolamine, adducts of 4-8 moles of ethylene oxide and/or propylene oxide with ethylene diamine and the like, and polyamines such as methylene bis(o-chloroaniline), ethylenediamine, ammonia and the like. Most preferred, on the basis of its optimum reactivity, is diethanolamine. "Chain extenders", for the purposes of this invention, are compounds having two active hydrogen-containing groups per molecule and an equivalent weight from about 31 to about 300, preferably about 31 to about 150. Hydroxyl-containing chain extenders include the alkylene glycols and glycol ethers such as ethylene glycol, 1,3-propylene glycol, 1,4-butylene glycol, 1,6-hexamethylene glycol, diethylene glycol, triethylene glycol, dipropylene glycol, tripropylene glycol, 1,4-cyclohexanedimethanol, alkoxylated aniline and the like. Amine chain extenders include diethyltoluene diamine, phenylene diamine, methylene bis(o-chloroaniline), NaCl blocked methylene bis(aniline), toluene diamine, aromatic diamines which are substituted at at least one of the carbon atoms adjacent to the amine groups with a lower alkyl group, and the like. Such chain extenders and crosslinkers, when used, are advantageously employed in a minor amount, i.e., less than about 50 parts by weight per 100 parts by weight polyol. Most preferably, the combined weight of chain extender and crosslinker is less than about 20, preferably less than about 5 parts by weight per 100 parts by weight polyol.

In addition to the foregoing components, additional materials such as colorants, cell openers, flame retardants, antioxidants, mold release agents, UV stabilizers, reinforcing agents and the like, which may vary according to the desired attributes of the foam, can be used in preparing foam according to this invention.

Foam is prepared according to this invention by mixing the foregoing components and permitting same to react. It is possible to employ a two-step technique whereby all or a major portion of the polyol is reacted with the polyisocyanate in a first step to form an isocyanate-terminated prepolymer, which is then reacted with the remaining components in a second step to form a foam. However, it is more preferred to employ a one-shot technique wherein all components are contacted and reacted in a single step.

In preparing molded foam in a one-shot process, all components except the polyisocyanate are advantageously blended together and fed as a single stream into a mixing head. However, certain components such as the volatile blowing agent are sometimes blended with the polyisocyanate. In addition, separate water, polyol, surfactant, etc. streams can be introduced on demand, if desired. The polyisocyanate advantageously is added to the mixing head as a separate stream where it is mixed with the polyol mixture and injected into the mold. In performing the mixing and mold filling steps, conventional, low pressure apparatus can be used, or high pressure impingement mixing processes, such as a reaction injection molding process, can be used. Generally, the components are mixed at approximately room temperature, although components such as pure MDI which are solid at room temperature may be heated above their melting points.

In one molding technique (hot molding process), the reactants are placed into a mold which is near ambient temperature. After filling, the mold is placed into an oven at a temperature of about 150° to about 300° C. to effect curing. In a second technique (cold molding process), the reactants are placed into a mold which is preheated to about 30° to about 75° C. After the mold is filled, it is placed in a 70°-200° C. oven to effect cure. In a third technique, the filled mold is maintained at ambient temperature during the curing process. In this third technique, the mold may or may not be preheated, although it preferably is to prevent heat sink effects.

A sufficient amount of the reaction mixture is placed into the mold so that, after expansion, the mixture completely fills the mold. Advantageously, a small excess of material is added over that minimally required to fill the mold. After filling the mold, the reaction mixture is permitted to cure in the mold at least to a state which permits the molded foam to be removed from the mold without permanent undesired distortion. In typical commercial procedures, an in-mold cure time of about 2 to about 30, preferably about 2 to about 15 minutes is adequate for this purpose. If required, the foam can be postcured by heating to about 50° to about 120° C. for a period of about 10 minutes to about 24 hours, preferably about 20 minutes to about 2 hours.

It may be necessary or desirable to mechanically open the cells of the foam during or after cure. This can be done by crushing the foam, puncturing the foam, vacuum crushing the foam, or by releasing the pressure in the mold at a proper stage of cure as taught in U.S. Pat. No. 4,579,700, incorporated herein by reference.

The benefits of this invention are particularly seen in preparing slabstock foam. Slabstock is often desirably of low density, requiring larger amounts of blowing agent, and is usually made in large buns, so that internal temperatures due to the exotherm from the reaction are particularly high. Both of these factors place great demands on the volatile blowing agent. In the commercial production of slabstock foam, the components can be and typically are introduced individually to a mixing head where they are thoroughly blended and metered onto a bed where foaming takes place. However, preblending of the components, except for the polyisocyanate, can be done if desired. The components are advantageously at room temperature or a slightly elevated temperature when blended in the mixing head, although preheating may be necessary in some instances to melt components which are solid at room temperature. After mixing the components and dispensing the mixture onto a bed, the mixture is permitted to freely rise and cure. After initial cure, the resulting bun can be trimmed and permitted to age for a short period to further develop physical properties.

The foam of this invention is useful in a wide range of cushioning and energy-absorbing applications, including, for example, bedding, furniture cushioning, padding, carpet underlayment, attached cushion carpet backing, automobile head rests, crash pads, arm rests, console covers, head liners, seating and the like.

The following examples are given to illustrate the invention and should not be interpreted as limiting it in any way. Unless stated otherwise, all parts and percentages are given by weight.

EXAMPLE 1

Slabstock foam Sample No. 1 and Comparative Sample A are prepared from the formulations set out in Table 1 following. In preparing the foam, all components except the polyisocyanate are thoroughly mixed, and to this mixture is added the polyisocyanate. The resulting mixture is immediately poured into an open 15"×15"×10" box and permitted to freely rise. In both cases, complete rise and blow off (indicating the opening of cells) occurs within about 115-135 seconds after isocyanate addition. The foam is permitted to age overnight to complete curing, and then cut into test samples, which are aged for seven days under controlled temperature and humidity conditions for physical property testing. Results of the physical property testing are as indicated in Table 2 following.

TABLE 1

| Component | Parts by Weight | |
|---|---|---|
| | Comparative Sample A* | Sample No. 1 |
| Polyol A[1] | 100 | 100 |
| Silicone Surfactant[2] | 1.48 | 1.48 |
| Amine Catalyst[3] | 0.08 | 0.08 |
| Stannous Octoate | 0.4 | 0.6 |
| Water | 3.47 | 3.47 |
| Methylene chloride | 13.25 | 0 |
| 1,1,1-Trichloroethane | 0 | 20.74 |
| TDI (index) | 102 | 102 |

*Not an example of this invention.
[1] A 1264 equivalent weight, nominally trifunctional random copolymer of about 88% propylene oxide and about 12% ethylene oxide.
[2] L560, from Union Carbide Corporation.
[3] D8264, from Air Products and Chemicals, Inc.

TABLE 2

| Property | Sample or Comparative Sample | |
|---|---|---|
| | A* | 1 |
| Rise Time, sec | 133 | 116 |
| Air Flow, ft³/min | 2.4 | 2.2 |
| Density, pcf | 1.31 | 1.43 |
| Tensile Str., psi[1] | 10.2 | 14.6 |
| Elongation, %[1] | 236 | 330 |
| Tear Resistance, pli[1] | 2.4 | 3.1 |
| Compression Set, 90%[1] | 3.3% | 6.2% |
| 25% IFD, pounds[1] | 24 | 23 |
| 65% IFD, pounds[1] | 42 | 42 |
| return 25% IFD, pounds[1] | 16 | 16 |
| Hysteresis Return, %[1] | 66.6 | 67.7 |

*Not an example of this invention.
[1] ASTM D-3574-81

As can be seen from the data in Table 2, the foam prepared in accordance with this invention has properties not significantly different than those of the control. This is considered very surprising in that 1,1,1-trichloroethane is the sole auxiliary blowing agent, and the size of the foam is small, so that the exotherm from the reaction is not great. It would be expected that the 1,1,1-trichloroethane would not adequately vaporize under these conditions. However, not only does complete blowing occur, but equivalent foam properties are obtained.

EXAMPLE 2

In the same manner as reported in Example 1, foam Sample No. 2 and Comparative Sample B are prepared from the formulations described in Table 3. Their physical properties are as reported in Table 4. Again, essentially equivalent properties are obtained using 1,1,1-trichlorethane as the sole auxiliary blowing agent

TABLE 3

| | Parts by Weight | |
|---|---|---|
| Component | Comparative Sample B* | Sample No. 2 |
| Polyol B [1] | 100 | 100 |
| Silicone Surfactant [2] | 1.1 | 1.1 |
| Amine Catalyst [3] | 0.058 | 0.058 |
| Stannous Octoate | 0.3 | 0.3 |
| Water | 5.4 | 5.4 |
| Methylene chloride | 13.25 | 0 |
| 1,1,1-Trichloroethane | 0 | 20.74 |
| TDI (index) | 108 | 108 |

*Not an example of this invention.
[1] An 1030 equivalent weight, nominally trifunctional random copolymer of about 88% propylene oxide and about 12% ethylene oxide.
[2] L-562, from Union Carbide Corporation.
[3] D8264, from Air Products and Chemicals, Inc.

TABLE 4

| | Sample or Comparative Sample | |
|---|---|---|
| Property | B* | 2 |
| Rise Time, sec | 107 | 103 |
| Air Flow, ft3/min | 1.6 | 1.7 |
| Density, pcf | 0.90 | 0.94 |
| Tensile Str., psi [1] | 12.1 | 12.6 |
| Elongation, % [1] | 156 | 165 |
| Tear Resistance, pli [1] | 1.7 | 1.8 |
| Compression Set, 90% [1] | 18.3% | 11.0% |
| 25% IFD, pounds [1] | 35 | 36 |
| 65% IFD, pounds [1] | 57 | 59 |
| return 25% IFD, pounds [1] | 20 | 20 |
| Hysteresis Return, % [1] | 55 | 56 |

*Not an example of this invention.
[1] ASTM D-3574-81

EXAMPLE 3

An ultra-low density, very high water foam (Sample No. 3) using 1,1,1-trichloroethane as an auxiliary blowing agent is prepared from the formulation in Table 5, following the general procedure described in Example 1. The resulting foam has properties comparable to a similar foam made using methylene chloride as an auxiliary blowing agent.

TABLE 5

| Component | Parts By Weight |
|---|---|
| Polyol B [1] | 100 |
| Silicone Surfactant [2] | 8 |
| Amine Catalyst [3] | 0.16 |
| Stannous Octoate | 2.25 |
| Water | 8.0 |
| 1,1,1-Trichloroethane | 35 |

TABLE 5-continued

| Component | Parts By Weight |
|---|---|
| TDI (parts by weight) | 92.7 |

[1] Same as [1] in Table 3.
Q2-5160, from Dow Corning Corporation.
C232, from Union Carbide Corporation.

EXAMPLE 4

Foam Sample Nos. 4-6 are prepared following the general procedure described in Example 1, using the formulations described in Table 6 following. The physical properties of the foams are as reported in Table 7. Again, good quality foam is obtained.

TABLE 6

| | Parts by Weight | | |
|---|---|---|---|
| Component | Sample No.4 | Sample No.5 | Sample No.6 |
| Polyol B [1] | 100 | 100 | 100 |
| Silicone Surfactant [2] | 1.1 | 1.1 | 1.1 |
| Amine Catalyst [3] | 0.058 | 0.058 | 0.058 |
| Stannous Octoate | 0.45 | 0.38 | 0.35 |
| Water | 5.4 | 5.4 | 5.4 |
| Methylene chloride | 7.92 | 6.6 | 0 |
| 1,1,1-Trichloroethane | 8.8 | 10.37 | 7.5 |
| ethyl chloride | 0 | 0 | 7.5 |
| TDI (index) | 108 | 108 | 108 |

[1]–[3] Same as [1]–[3] in Table 3.

TABLE 7

| | Sample No. | | |
|---|---|---|---|
| Property | 4 | 5 | 6 |
| Rise Time, sec | 95 | 100 | 114 |
| Air Flow, ft3/min | 0.58 | 1.7 | 0.5 |
| Density, pcf | 0.88 | 0.92 | 0.87 |
| Tensile Str., psi [1] | 12.4 | 13.3 | 13.2 |
| Elongation, % [1] | 161 | 175 | 178 |
| Tear Resistance, pli [1] | 1.8 | 1.9 | 1.5 |
| Compression Set, 90% [1] | 29.0 | 10.0 | 13.8 |
| 25% IFD, pounds [1] | 37 | 35 | 36 |
| 65% IFD, pounds [1] | 59 | 58 | 57 |
| return 25% IFD, pounds [1] | 20 | 20 | 19 |
| Hysteresis Return, % [1] | 1.61 | 1.64 | 1.58 |

[1] ASTM D-3574-81

What is claimed is:

1. A process for preparing flexible foam comprising reacting a reaction mixture comprising a polyisocyanate and a relatively high equivalent weight active hydrogen-containing material in the presence of a volatile blowing agent, wherein at least about 85 mole percent of said volatile blowing agent is 1,1,1-trichloroethane and the remaining being another volatile blowing agent having a boiling point of at least −15° C. at 1 atmosphere pressure but below the maximum temperatures generated during the reaction to form the foam.

2. The process of claim 1 wherein said relatively high equivalent weight active hydrogen-containing material is a polyether.

3. The process of claim 2 wherein said reaction mixture further comprises water.

4. The process of claim 3 wherein said polyether is hydroxyl-terminated and nominally has an average of about 2 to about 4 hydroxyl groups per molecule.

5. The process of claim 4 in which the reaction mixture freely rises.

6. The process of claim 5 wherein the polyisocyanate is toluene diisocyanate or a prepolymer thereof.

7. The process of claims 6 wherein 1,1,1-trichloroethane constitutes at least about 95 mole percent of the volatile blowing agent.

8. The process of claim 7 wherein said volatile blowing agent consists essentially of 1,1,1-trichloroethane.

9. The process of claim 7 wherein said reaction mixture further comprises a silicone surfactant and a organometallic catalyst.

10. The process of claim 9 wherein the reaction mixture contains about 2 to about 8 parts by weight water per 100 parts by weight polyether and about 20 to about 40 parts by weight 1,1,1-trichloroethane.

11. The process of claim 4 in which the reaction mixture reacts in a closed mold.

12. The process of claim 11 wherein said volatile blowing agent consists essentially of 1,1,1-trichloroethane.

13. A process for preparing flexible foam comprising reacting a reaction mixture comprising a polyisocyanate and a relatively high equivalent weight active hydrogen-containing material in the presence of a volatile blowing agent, wherein the volatile blowing agent is a mixture of at least about 50 weight percent 1,1,1-trichloroethane, from about 0 to about 50 weight percent ethyl chloride or methylene chloride or mixtures thereof, and from about 0 to about 15 weight percent of another volatile blowing agent having a boiling point of at least $-15°$ C. at 1 atmosphere pressure but below the maximum temperature generated during the reaction to form the foam.

14. The process of claim 13 wherein said relatively high equivalent weight active hydrogen-containing material is a polyether.

15. The process of claim 14 wherein said reaction mixture further comprises water.

16. The process of claim 15 wherein said polyether is hydroxyl-terminated and nominally has an average of about 2 to about 4 hydroxyl groups per molecule.

17. The process of claim 16 wherein said volatile blowing agent is about 50-85 weight percent 1,1,1-trichloroethane and about 15-50 weight percent methylene chloride.

18. The process of claim 16 wherein said volatile blowing agent is about 50-85 weight percent 1,1,1-trichloroethane and about 15-50 weight percent ethyl chloride.

19. The process of claim 16 wherein the reaction mixture contains about 2 to about 5 parts of water per 100 parts by weight polyether.

20. The process of claim 1 wherein said volatile blowing agent having a boiling point of at least $-15°$ C. is selected from the group consisting of methylene chloride, ethyl chloride, CFC-11, CFC-113, CFC-114, CFC-123, CFC-123a, CFC-124, CFC-124a, CFC-133 (all isomers), CFC-134, CFC-134a, CFC-141b, CFC-142, CFC-151, pentane, heptane, hexane, perhalogenated propanes and mixtures thereof.

21. The process of claim 13 wherein said volatile blowing agent having a boiling point of at least $-15°$ C. is selected from the group consisting of CFC-11, CFC-113, CFC-114, CFC-123, CFC-123a, CFC-124, CFC-124a, CFC-133 (all isomers), CFC-134, CFC-134a, CFC-141b, CFC-142, CFC-151, pentane, heptane, hexane, perhalogenated propane.

* * * * *